(12) United States Patent
Barker et al.

(10) Patent No.: US 8,465,203 B2
(45) Date of Patent: Jun. 18, 2013

(54) BRAKE SYSTEMS FOR C-ARM POSITIONING DEVICES, APPARATUS CONTAINING THE SAME AND METHODS FOR USING SUCH SYSTEMS

(75) Inventors: David Barker, Salt Lake City, UT (US); John Matthew Simmons, Bountiful, UT (US); Jan Bruening, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 292 days.

(21) Appl. No.: 13/039,076

(22) Filed: Mar. 2, 2011

(65) Prior Publication Data

US 2012/0224673 A1  Sep. 6, 2012

(51) Int. Cl.
  *H05G 1/02*  (2006.01)
(52) U.S. Cl.
  USPC .......................................................... 378/197
(58) Field of Classification Search
  USPC .................................................. 378/193–198
  See application file for complete search history.

(56) References Cited

U.S. PATENT DOCUMENTS

| 5,627,873 A | 5/1997 | Hanover et al. ............... 378/197 |
| 6,007,243 A | 12/1999 | Ergun et al. ................... 378/197 |
| 6,234,672 B1 | 5/2001 | Tomasetti et al. ............. 378/197 |

*Primary Examiner* — Courtney Thomas
(74) *Attorney, Agent, or Firm* — Kenneth E. Horton; Kirton McConkie

(57) ABSTRACT

Systems and methods for using a brake system to selectively lock and release the vertical motion of a C-arm X-ray device that is part of a sliding counterbalanced C-arm positioning device are described. In such systems and methods, the C-arm positioning device typically includes a C-arm X-ray device, a linear bearing rail assembly, a linear bearing block, a counterbalance mechanism, and brake system. Generally, the C-arm is connected to the linear bearing block, which is slidably coupled to the bearing rail assembly to allow the bearing block and C-arm to slide up and down on the rail assembly. The counterbalance mechanism applies a force to the bearing block to substantially counterbalance the weight of the components, such as the C-arm, that are suspended from the bearing block. The brake system can be actuated to engage the linear bearing rail assembly and lock the vertical movement of the linear bearing block. Other embodiments are described.

25 Claims, 12 Drawing Sheets

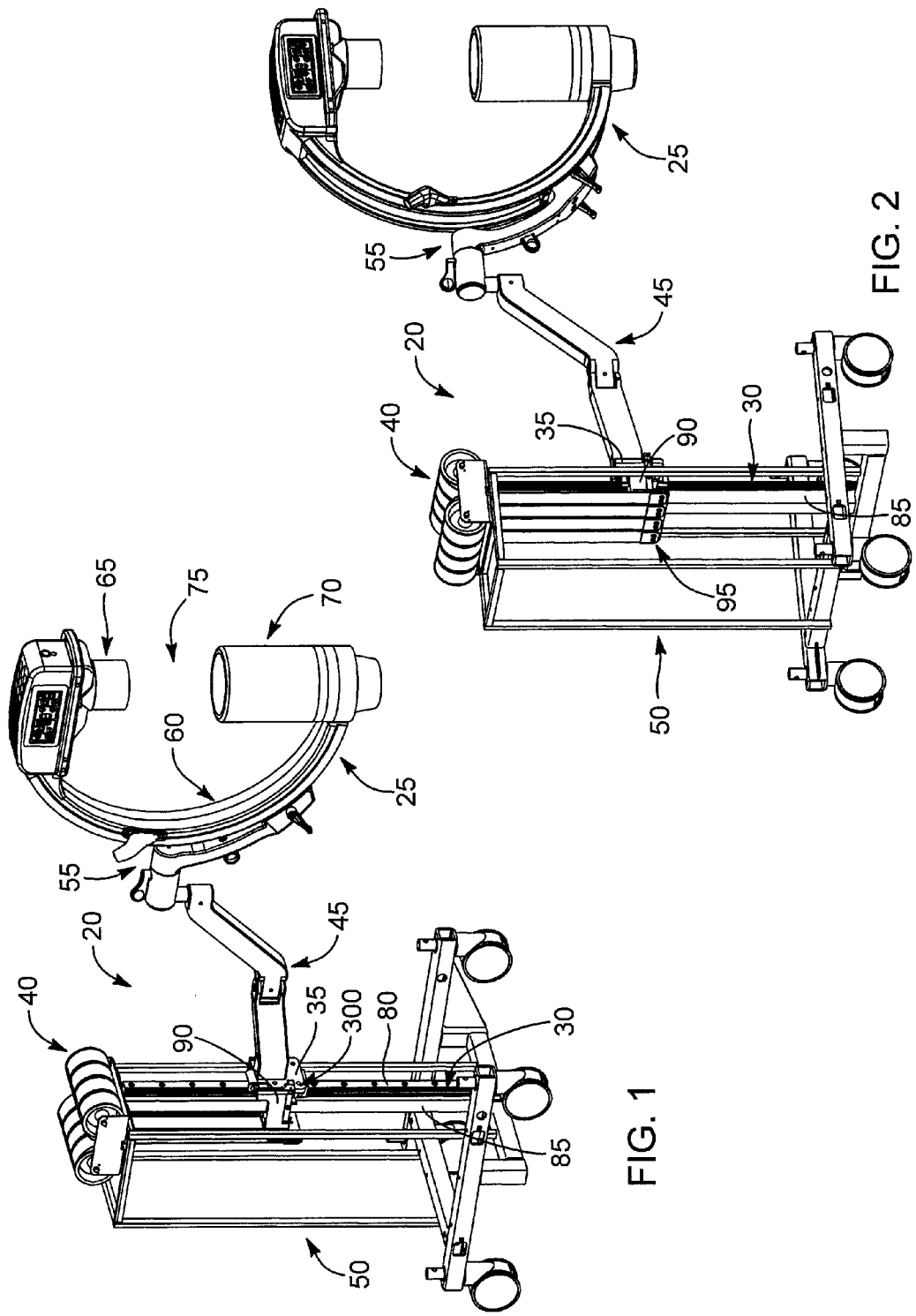

BRAKE SYSTEMS FOR C-ARM POSITIONING DEVICES, APPARATUS CONTAINING THE SAME AND METHODS FOR USING SUCH SYSTEMS

FIELD

This application relates generally to X-ray equipment. More specifically, this application relates to systems and methods for using a brake system to selectively lock and release the vertical movement of a C-arm X-ray device that is disposed on a sliding counterbalanced C-arm positioning device.

BACKGROUND

X-ray machines are known devices that allow individuals, such as healthcare practitioners, to capture images, in a relatively non-intrusive manner, of bones, bone density, implanted devices, catheters, pins, and a wide variety of other objects and materials that are within a patient's body. In this regard, the term X-ray may refer to any suitable type of X-ray imaging, including film X-ray shadowgrams and X-ray fluoroscopic imaging, which may refer to images that are produced by the conversion of an incident X-ray pattern to a "live" enhanced or intensified optical image that can be displayed on a video monitor, nearly contemporaneously with the irradiation of the portion of the patient's body that is being imaged.

Often, when a practitioner takes X-rays of a patient, it is desirable to take several X-rays of one or more portions of the patient's body from a number of different positions and angles, and preferably without needing to frequently reposition the patient. To meet this need, C-arm X-ray diagnostic equipment has been developed. The term C-arm generally refers to an X-ray imaging device having a rigid and/or articulating structural member having an X-ray source and an image detector assembly that are each located at an opposing end of the structural member so that the X-ray source and the image detector face each other. The structural member is typically "C" shaped and so is referred to as a C-arm. In this manner, X-rays emitted from the X-ray source can impinge on the image detector and provide an X-ray image of the object or objects that are placed between the X-ray source and the image detector.

In many cases, C-arms are connected to one end of a movable arm. In such cases, the C-arm can often be raised and lowered, be moved from side to side, and/or be rotated about one or more axes of rotation. Accordingly, such C-arms can be moved and reoriented to allow X-ray images to be taken from several different positions and angles and different portions of a patient, without requiring the patient to be frequently repositioned.

SUMMARY

This application relates generally to X-ray positioning devices. In particular, this application relates to systems and methods for using a brake system to selectively lock and release the vertical motion of a C-arm X-ray device that is part of a sliding counterbalanced C-arm positioning device. In such systems and methods, the C-arm positioning device typically comprises a C-arm X-ray device, a linear bearing rail assembly, a linear bearing block, a counterbalance mechanism, and the brake system. Generally, the C-arm can be connected to the linear bearing block which can be slidably coupled to the bearing rail assembly to allow the bearing block and C-arm to slide up and down on the linear bearing rail assembly. The counterbalance mechanism can be configured to apply a force to the bearing block to substantially counterbalance the weight of the components, such as the C-arm, that are suspended from the bearing block. In some configurations, the brake system can be actuated to physically engage the linear bearing rail assembly and, thereby, selectively lock the vertical movement of the linear bearing block and the C-arm.

BRIEF DESCRIPTION OF THE DRAWINGS

The following description can be better understood in light of the Figures, in which:

FIG. 1 shows a front perspective view of some embodiments of a sliding C-arm positioning device having a counterbalance mechanism that is partially disposed above a linear bearing block;

FIG. 2 shows a side perspective view of the C-arm positioning device of FIG. 1;

Figure 3A:
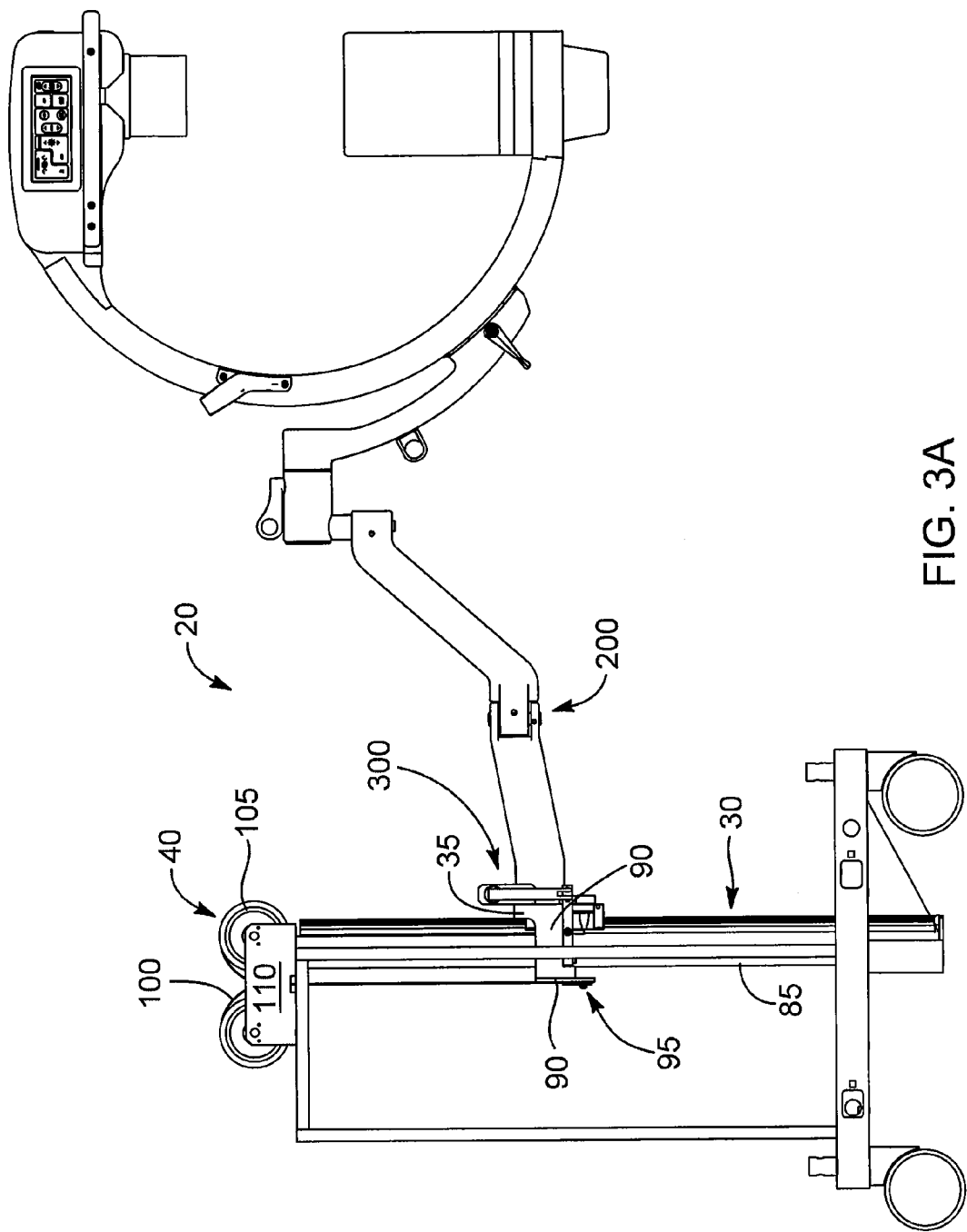
FIG. 3A shows a side plan view of the C-arm positioning device of FIG. 1.

The Figures illustrate specific aspects of the described brake systems for C-arm positioning devices and methods for making and using such systems. Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

The following description supplies specific details in order to provide a thorough understanding. Nevertheless, the skilled artisan will understand that the described brake systems for C-arm positioning devices and associated methods of making and using the brake systems can be implemented and used without employing these specific details. Indeed, the described brake systems for C-arm positioning devices and associated methods can be placed into practice by modifying the described systems and methods and can be used in conjunction with any other apparatus and techniques conventionally used in the industry. For example, while the description below focuses on methods for making and using the brake systems for C-arm positioning devices that comprise a mini C-arm, the brake systems can be used on a C-arm positioning device comprising virtually any other type of X-ray equipment, including standard C-arm devices.

The present application describes brake systems that allow a user to selectively stop and release the vertical movement of a C-arm X-ray assembly that is part of a C-arm positioning device. The brake systems can be used with any type of imaging arm, including an O-arm or a C-arm. In some embodiments, the positioning device can be used with C-arm devices. While the described brake systems can be used on any suitable C-arm positioning device, the following description focuses on using the brake systems on a sliding counterbalanced C-arm positioning device. To provide a better understanding of the described brake systems for C-arm positioning devices, the following discussion first describes some embodiments of a suitable sliding counterbalanced C-arm positioning device that can incorporate the brake systems. Following that discussion, a more detailed description of the described brake systems is provided.

As mentioned above, the described brake systems for C-arm positioning devices can be used with any suitable C-arm positioning device. FIG. 1 shows some embodiments in which the brake system 300 (shown also in FIG. 11) is used with a sliding counterbalanced C-arm positioning device (or C-arm positioning device) 20. While such a C-arm positioning device can comprise any suitable component, FIG. 1 shows some embodiments in which the illustrated embodiments of the C-arm positioning device 20 comprise a C-arm X-ray assembly (or C-arm) 25, a linear bearing rail assembly 30, a linear bearing block 35, and a counterbalance mechanism 40. FIG. 1 also shows that, in some embodiments, the C-arm positioning device 20 optionally comprises a C-arm support arm 45, a bearing rail support structure 50, and/or a C-arm rotational system 55.

The C-arm 25 can comprise any suitable C-arm that allows the C-arm positioning device 20 to be used to take X-ray images of a portion of a patient's body (not shown). For example, the C-arm can comprise a mini C-arm, a standard C-arm, and/or any other suitable type of C-arm X-ray assembly. By way of illustration, FIG. 1 shows some embodiments in which the C-arm 25 comprises a mini C-arm 60.

The C-arm 25 can also comprise any suitable component that allows it to function as intended. For example, FIG. 1 shows some embodiments in which the C-arm 25 comprises an X-ray source 65 and an X-ray image detector 70 that are respectively disposed at nearly opposite ends of the C-arm so as to face each other. The X-ray image detector can be any known detector, including a digital flat panel detector or an image intensifier. FIG. 1 also shows that the X-ray source 65 and image detector 70 are spaced apart to define a gap 75 that is large enough to allow a portion of a patient's body (e.g., a limb, an extremity, etc.) to be inserted into the path of the X-ray beam (not shown) for X-ray imaging.

The linear bearing rail assembly 30 can serve any suitable purpose, including providing a guide, support, and/or rail on which the linear bearing block 35 (described below) and C-arm 25 can slide in two directions (e.g., vertically up and down). In this regard, the linear bearing rail assembly can comprise any suitable component that allows the assembly to function as intended. By way of illustration, FIG. 1 shows some embodiments in which the linear bearing rail assembly 30 comprises a linear bearing rail 80 and optionally comprises a linear bearing rail spine 85.

The linear bearing rail 80 can comprise any known or novel linear bearing rail that can be coupled to the linear bearing block 35 in a manner that allows the bearing block and C-arm 25 to be raised and lowered in the manner described herein. Indeed, some examples of suitable linear bearing rails include one or more conventional or novel T-rails, U-rails, T+U rails, V-rails, monorails, telescopic drawer slides, linear slides, curved bearing rails, roller embossed rails, round shaft rails (i.e., single rail, double rail, etc.), square shaft rails (i.e., single rail, double rail, etc.), and/or any combination thereof. By way of illustration, FIG. 1 shows some embodiments of the linear bearing rail 80.

The linear bearing rail 80 can have any suitable characteristic that allows it to fulfill its intended purpose. In one example, the linear bearing rail can comprise one or more grooves that are sized and shaped to receive rollers (e.g., wheels, bearings, etc.) from the linear bearing block 35. In another example, the linear bearing rail comprises one or more raised rails that fit within one or more corresponding roller mechanisms (e.g., one or more wheels, bearing raceways, etc.) of the linear bearing block. In still another example, the linear bearing rail 80 can be any suitable length. Indeed, in some embodiments, the linear bearing rail can be a length selected from about 10 inches, about 24 inches, about 34 inches, about 48 inches, about 56 inches, about 120 inches, and any suitable combination or sub-range of the these lengths. For instance, some embodiments of the linear bearing rail can be between about 24, about 36, and about 48 inches (e.g., 34±5 inches).

Where the linear bearing rail assembly 30 comprises a spine 85, the spine can serve any suitable purpose, including physically supporting the linear bearing rail 80 and/or providing a braking surface for the brake system 300. Moreover, where the linear bearing rail assembly includes the spine, the spine can comprise any suitable component that is capable of physically supporting the linear bearing rail and/or providing a braking surface. By way of example, the spine can comprise a solid shaft, a hollow pipe, a rail, a sheet of rigid material, a column, and/or any other suitable support.

The linear bearing block 35 can serve any suitable purpose, including slidably attaching the C-arm 25 to the linear bearing rail 80 to allow the C-arm to be moved in two directions (e.g., substantially vertically up and down). Accordingly, the linear bearing block can comprise any suitable component that allows it to slidably couple with the linear bearing rail and to connect to and support the weight of one of the described brake systems, the C-arm, and/or any other suitable components. Indeed, in some embodiments, the linear bearing block comprises one or more rollers (e.g., bearings, wheels, ball guides with balls, linear ball bearings, etc.). Moreover, in some embodiments, the linear bearing block is configured to slidably couple with the linear bearing rail by having one end of the rail be inserted into the linear bearing block.

Because the linear bearing rail 80 can be any suitable length (as discussed above), the linear bearing block 35 can have any suitable maximum range of movement, or stroke. Indeed, in some implementations, the linear bearing block has a stroke that is substantially equal to the length of the linear bearing rail less the height of the linear bearing block. Accordingly, in some embodiments, the linear bearing block has a stroke with a length selected from about 10 inches, about 12 inches, about 24 inches, about 36 inches, about 48 inches, about 60 inches, about 80 inches, about 100 inches, and about 120 inches. In this regard, the linear bearing block can have any suitable stroke that falls within any suitable combination or sub-range of the aforementioned stroke lengths. For instance, some embodiments of the C-arm positioning device have a linear bearing block having a stroke that is greater than about 24 and less than about 48 inches (e.g., about 36±5 inches). In still other embodiments, the linear bearing block has a stroke that is longer than about 32 inches (e.g., longer than about 34 inches) and less than about 44 inches.

The linear bearing block 35 can also comprise any other suitable component or characteristic that allows it to function as intended. For instance, FIGS. 1 and 2 shows some embodiments in which the linear bearing block 35 comprises a carriage 90. In such embodiments, the carriage can perform any suitable function, including serving as a connection point for the counterbalance mechanism 40, the brake system 300, and/or any other suitable component. To this end, the carriage can have any suitable characteristic that allows it to perform its intended functions. For example, FIG. 3A shows that the carriage 90 can wrap around at least a portion of the linear bearing rail assembly 30 and serve to support the brake system 300 and as a connection point 95 for the counterbalance mechanism 40 on the linear bearing block.

The counterbalance mechanism 40 can serve any suitable purpose. Indeed, in some embodiments, the counterbalance mechanism applies a force to the linear bearing block 35 (directly or indirectly) to counterbalance at least a portion of the weight of the linear bearing block, the C-arm 25, the brake system 300, and/or any other component or components of the C-arm positioning device 20 that rests their weight on the linear bearing block (e.g., the C-arm support arm 45, power cables, etc.), collectively referred to herein as the linear bearing block assembly 200.

Where the counterbalance mechanism 40 counterbalances the weight of the linear bearing block assembly 200, a user can raise or lower the C-arm 25 with relatively little effort. Furthermore, where the counterbalance mechanism counterbalances the weight of the linear bearing block assembly, the counterbalance mechanism can help maintain the position of the linear bearing block 35 with respect to the linear bearing rail 80. In this manner, the counterbalance mechanism can help prevent the linear bearing block from creeping down (due to the force of gravity on the linear bearing block assembly being greater than the upward force of the counterbalance mechanism on the linear bearing block) and from creeping up on the rail (due to the upward force of the counterbalance mechanism being greater than the force of gravity on the linear bearing block assembly).

The counterbalance mechanism 40 can comprise any suitable component that allows it to substantially counterbalance the weight of the linear bearing block assembly 200. Some examples of suitable counterbalance mechanisms comprise one or more constant force springs, spring motors, gas springs, tension springs, torsion springs, compression springs, cams, hydraulic circuits, weights, pulleys and a cable, and/or any other suitable component that allows the counterbalance mechanism to fulfill its intended purpose. In some embodiments, however, the counterbalance mechanism does not comprise a gas spring.

Figure 3B:
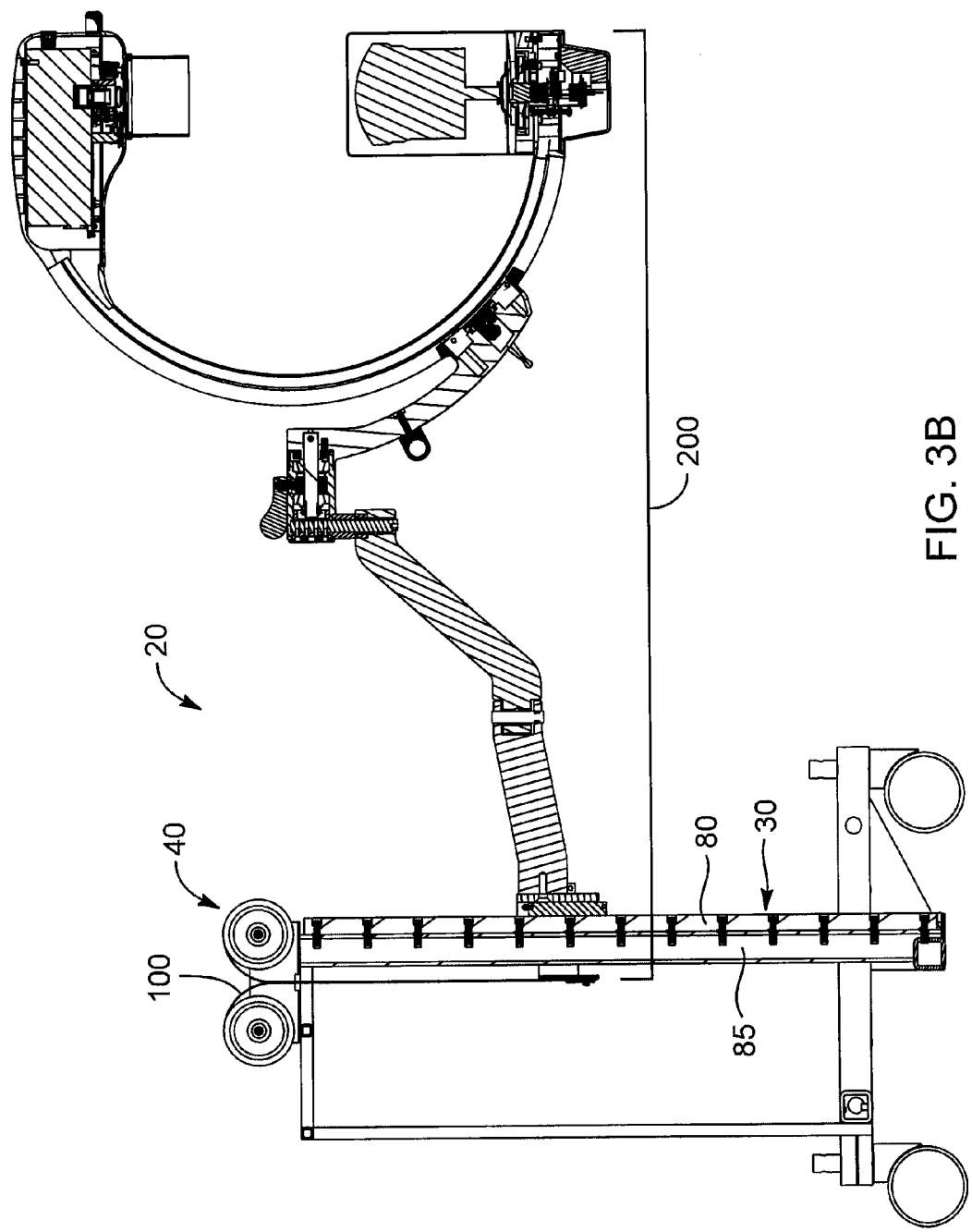
FIG. 3B shows a cross-sectional side view of the C-arm positioning device of FIG. 1.
Figure 4:
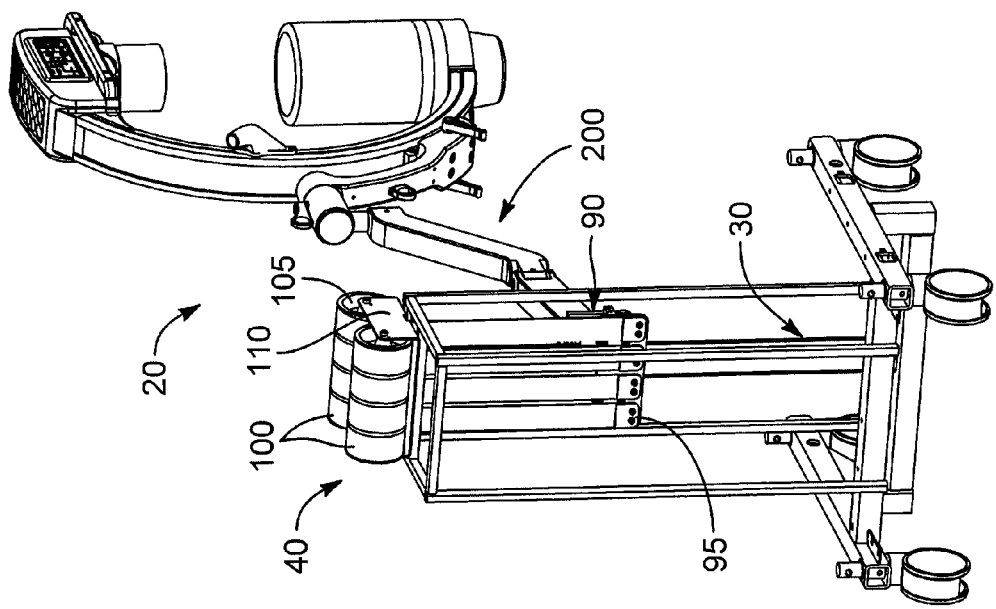
FIG. 4 shows a back perspective view of the C-arm positioning device of FIG. 1.

In one example of a suitable counterbalance mechanism 40, FIGS. 3A through 4 show some embodiments in which the counterbalance mechanism 40 comprises one or more constant force springs 100. A constant force spring may comprise virtually any suitable spring that exerts a substantially constant force over its range of motion. That said, in some embodiments, each of the constant force springs is generally constructed as a rolled ribbon of spring steel such that each of the springs is relaxed when it is fully coiled and tensed as it is uncoiled.

Where the counterbalance mechanism 40 comprises one or more constant force springs 100, the mechanism can comprise any suitable number of constant force springs that allows it to substantially counterbalance the weight of the linear bearing block assembly 200. For instance, the counterbalance mechanism can comprise 1, 2, 3, 4, 5, 6, 7, 8, . . . 20, or more constant force springs. Indeed, FIG. 4 shows some embodiments in which the counterbalance mechanism 40 comprises 8 constant force springs 100. In any case, in order to counterbalance the weight of the linear bearing block assembly, the total upward (or opposing) force that the springs exert on the linear bearing block 35 is substantially equal to the weight or mass of the linear bearing block assembly.

Where the counterbalance mechanism 40 comprises one or more constant force springs 100, the mechanism can also comprise any other suitable component that allows the C-arm positioning device 20 to function as intended. By way of illustration, FIG. 4 shows some embodiments in which each of the constant force springs 100 of the counterbalance mechanism 40 is configured to coil on a rotating spool 105 that is mounted to the C-arm positioning device 20 (e.g., via bracket 110). Furthermore, while the constant force springs can be assembled in the counterbalance mechanism in any suitable manner, FIG. 4 further shows some embodiments in which pairs of corresponding constant force springs 100 coil in opposite directions so that springs from a corresponding pair of coils can easily be connected to the same connection point 95.

Figure 5:
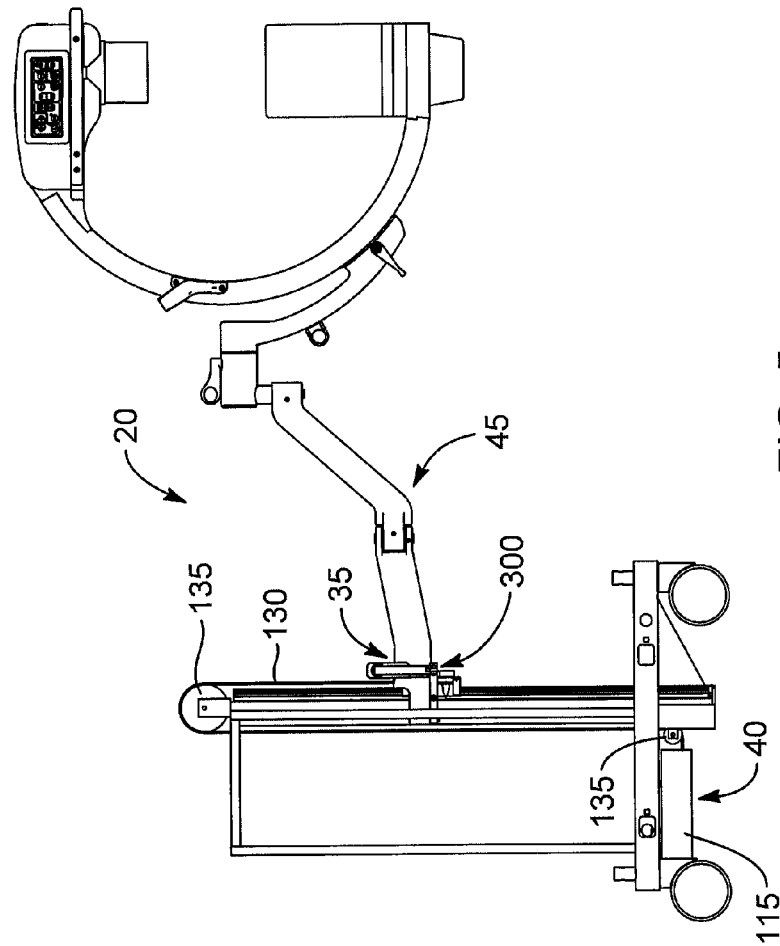
FIG. 5 shows a side plan view of some embodiments of a sliding C-arm positioning device having the counterbalance mechanism that is partially disposed below a linear bearing block.
Figure 6:
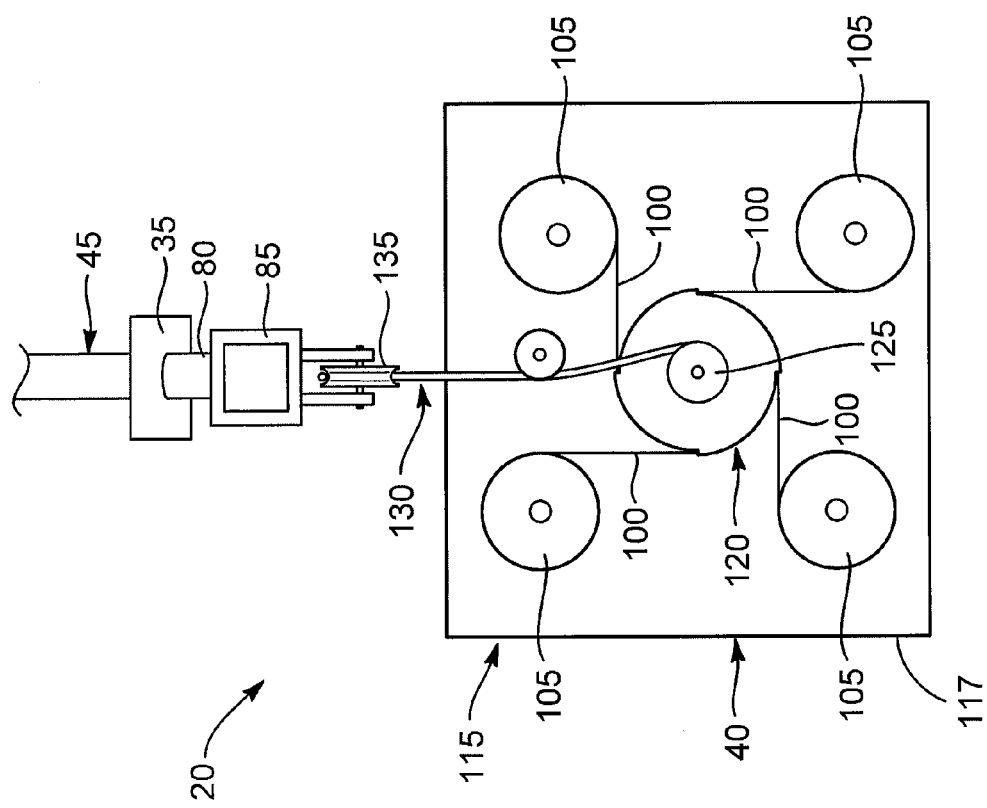
FIG. 6 shows a bottom plan view of some embodiments of a portion of the sliding C-arm positioning device that have a spring motor.

In another example of a suitable counterbalance mechanism 40, FIGS. 5 and 6 show some embodiments in which the counterbalance mechanism 40 comprises a spring motor 115. In such embodiments, the spring motor can have any suitable characteristic consistent with its function described herein. By way of illustration, FIG. 6 (which shows a bottom view of only some components of the C-arm positioning device 20 of FIG. 5) shows some embodiments in which the spring motor 115 comprises a housing 117 containing 4 constant force springs 100 that are each coiled around a rotating spool 105 and connected to a constant force spring drum 120, which, in turn, is fixed with respect to a flexible connector drum 125. In these embodiments, as the flexible connector (e.g., cable 130) is unwound from the flexible connector drum, the constant force springs are uncoiled from their respective constant force spools and are wound, at least partially, on the constant force spring drum—thus allowing the C-arm 25 to be lowered.

While FIG. 6 shows some embodiments of the spring motor 115 that comprise 4 constant force springs 100, the spring motor may be modified in any suitable manner that allows it to perform its intended function. For example, the spring motor can comprise 1, 2, 3, 5, 6, 7, 8, or more constant force springs, which are each attached to the constant force spring drum 120.

The counterbalance mechanism 40 can be disposed in any suitable location that allows it to function as intended. Indeed, while in some embodiments, the counterbalance mechanism is disposed at least partially above the linear bearing block 35, as shown in FIG. 4, in other embodiments, the counterbalance mechanism 40 can be located at least partially below or to the side of the linear bearing block, as shown in FIG. 5). In one example, FIG. 4 shows the counterbalance mechanism 40 is mounted above the linear bearing block 35 to allow the constant force springs 100 to coil above the linear bearing block. In another example, FIG. 4 shows the springs (not shown) of the mechanism 40 coil, at least partially, below the linear bearing block 35. In another example, which is not illustrated, the counterbalance mechanism is mounted on the linear bearing block (e.g., so as to coil at the block) and/or the C-arm support arm assembly 45.

Despite the location of the counterbalance mechanism 40, the mechanism can be connected to the linear bearing block 35 in any suitable manner that allows it to apply an upward force to the linear bearing block 35. In one example, springs 100 extending from the counterbalance mechanism are attached to the linear bearing block (directly or indirectly). By way of illustration, FIG. 4 shows some embodiments in which constant force springs 100 from the counterbalance mechanism 40 are attached to the linear bearing block 35 (e.g., via the carriage 90) at connection point 95.

In another example, the counterbalance mechanism 40 uses one or more flexible connectors (e.g., one or more cables, roller chains, belts, and/or any other suitable components) to apply a counterbalancing force to the linear bearing block 35. In this example, the C-arm positioning device 20 can optionally comprise one or more rotating wheels (e.g., pulleys, gears, spools, and/or any other suitable rotating components) to change the direction of the flexible connector so as to allow the counterbalance mechanism to apply an upward force to the linear bearing block, despite the mechanism's position. By way of illustration, FIG. 5 shows some embodiments in which a cable 130 extends between the spring motor 115 and the linear bearing block 35, using multiple pulleys 135 to redirect the cable.

In some embodiments, the C-arm 25 (or the C-arm rotational system 55) is connected directly to the linear bearing block 35, in other embodiments, the C-arm support arm 45 connects the C-arm to the linear bearing block. In these latter embodiments, the C-arm support arm can have any suitable component or characteristic. By way of example, the C-arm support arm can have any suitable number of elongated sections and can optionally have any suitable number or type of pivot joints. For instance, FIGS. 7 and 8 show some embodiments in which the C-arm support arm 45 comprises a first elongated section 140 and a second elongated section 145.

Where the C-arm support arm 45 comprises a first elongated section 140, that section can comprise any suitable component or characteristic. In one example, while the first elongated section can be pivotally attached to the linear bearing block 35, FIGS. 7 and 8 show some embodiments in which the first elongated section 140 is fixed in position with respect to the linear bearing block 35. In another example, FIGS. 7 and 8 show that the first elongated section 140 comprises a pivot joint 146 that pivotally attaches to the second elongated section 145 to allow the second elongated section to pivot horizontally through an arc of motion.

The second elongated section 145 can comprise any suitable component or characteristic. By way of illustration, FIGS. 7 and 8 show some embodiments in which the second elongated section 145 is pivotally connected to the C-arm rotational system 55 (e.g., via pivot joint 148) to allow the C-arm rotational system and C-arm 25 to pivot horizontally through an arc of motion.

Figure 7:
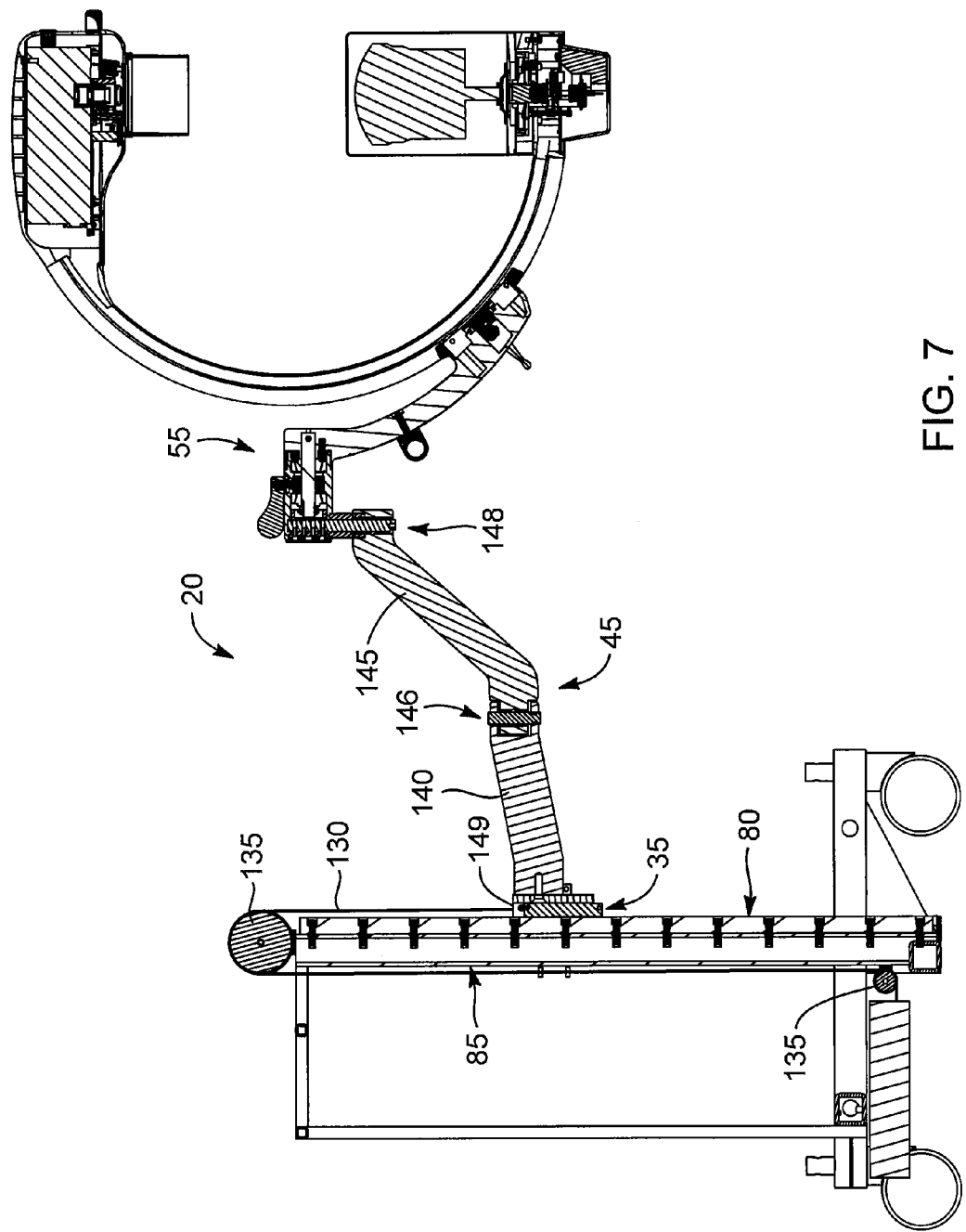
FIG. 7 shows a cross-sectional side view of the C-arm positioning device of FIG. 5.
Figure 8:
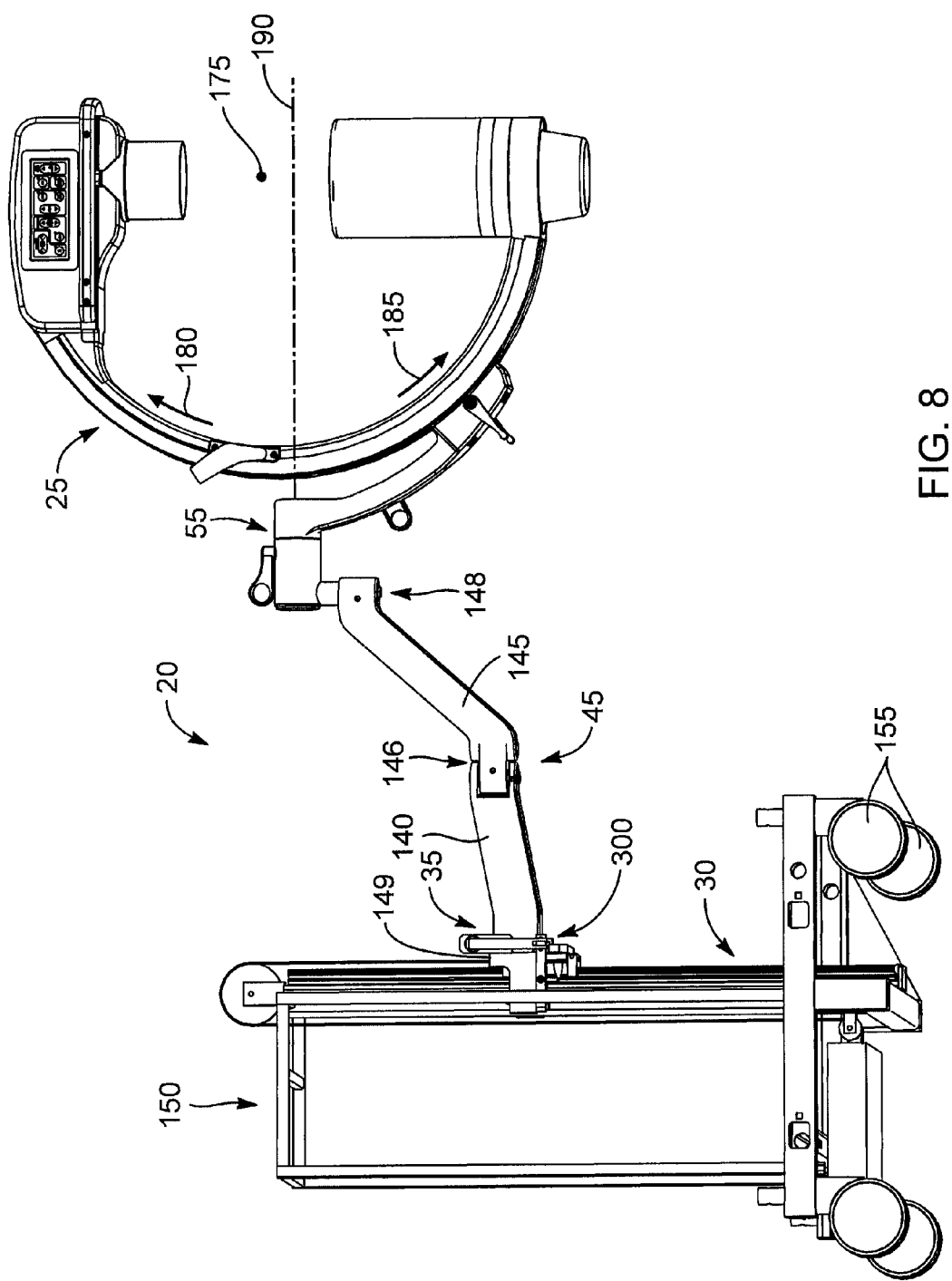
FIG. 8 shows a side perspective view of the C-arm positioning device of FIG. 5.

In another example of a suitable characteristic of the second elongated section 145, FIGS. 7 and 8 show that the second elongated section 145 is optionally permanently angled so as to rise above an upper edge 149 of the linear bearing block 35. In this manner, the second elongated member can allow the stroke of the linear bearing block to extend lower on the linear bearing rail 80 without allowing the C-arm to be damaged by allowing it to strike the floor (not shown).

In order to keep the linear bearing rail 80 in a desired orientation (e.g., substantially vertical), the linear bearing rail (and/or spine 85) can be connected to any suitable bearing rail support structure 50. Indeed, in some implementations, the linear bearing rail is connected to a fixed support structure, such as a wall, a column, a floor, a shelf, a cabinet, a stationary frame, and/or any other suitable support structure that is not intended to be easily moved and repositioned around a patient.

In other implementations, however, the linear bearing rail 80 (and/or spine 85) is connected to a movable support structure. In such implementations, the movable support structure can comprise any suitable characteristic that allows it to move across a floor while supporting the linear bearing rail and any objects supported therefrom (e.g., the linear bearing block assembly 200). Thus, the movable support structure can comprise one or more wheels, shelves, handles, weights to prevent the weight of the C-arm from tipping the movable support structure, and/or any other suitable components. By way of illustration, FIG. 8 shows some embodiments in which the movable support structure 150 comprises a wheeled framework that supports linear bearing rail assembly 30. FIG. 8 also shows some embodiments in which two of the wheels 155 extend past the linear bearing rail assembly 30 to prevent the weight of the C-arm 25 from causing the movable support structure 150 to tip.

As previously mentioned, the C-arm positioning device 20 can also comprise a C-arm rotational system 55. In this regard, the C-arm rotational system can comprise any known or novel C-arm rotational system that allows the C-arm to be repositioned on the linear bearing block 30 or at the end of the C-arm support arm 45. By way of illustration, FIG. 8 shows some embodiments in which the C-arm rotational system 55 is configured to allow the C-arm 25 to rotate orbitally about an axis of orbital rotation 175 in the direction of arrows 180 and 185, as well as to rotate around an axis of lateral rotation 190 to thereby rotate the C-arm 25 laterally.

Figure 9:
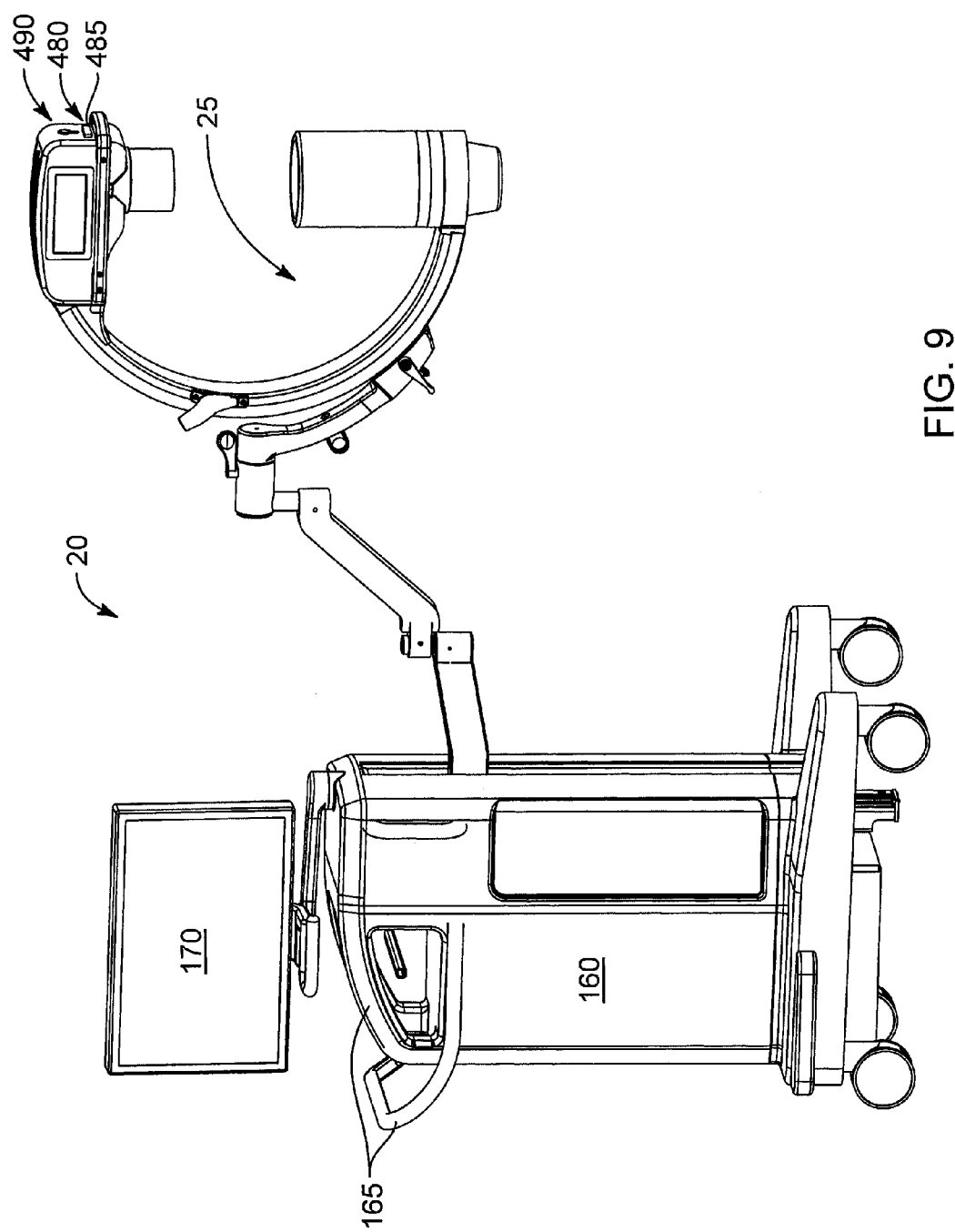
FIG. 9 shows a side perspective view of some embodiments of the C-arm positioning device comprising a cover and monitor.

In addition to the aforementioned components, the described C-arm positioning device 20 can comprise any other suitable component or characteristic known in the art. For example, the C-arm positioning device can comprise one or more support structure covers, monitors, handles, power supplies (e.g., internal (such as a uninterruptable power supply) and/or external power supplies), X-ray imaging systems, and/or X-ray control devices. By way of illustration, FIG. 9 shows some embodiments in which the C-arm positioning device 20 comprises a support structure cover 160, handles 165, and a monitor 170.

With reference now to the described brake systems 300 for C-arm positioning devices (e.g., C-arm positioning device 20), the brake systems can comprise any suitable type of break system that can selectively lock and unlock the vertical movement of the linear bearing block 35 (and hence the C-arm 25) with respect to the linear bearing rail 80. In some embodiments, the brake system can comprise any suitable brake system or component that is configured to physically engage and disengage the linear bearing rail assembly 30 (e.g., the linear bearing rail and/or spine 85) to selectively lock and unlock the vertical movement of the linear bearing block). Some examples of suitable types of brake systems 300 include frictional brake systems (e.g., a V-brake, dual-pivot caliper brake, single-pivot caliper brake, U-brake, cantilever brake, roller cam brake, delta break, etc.), and mechanical brake systems (e.g., a rack and pinion brake, ratchet brake, etc.).

Figures 10, 11:
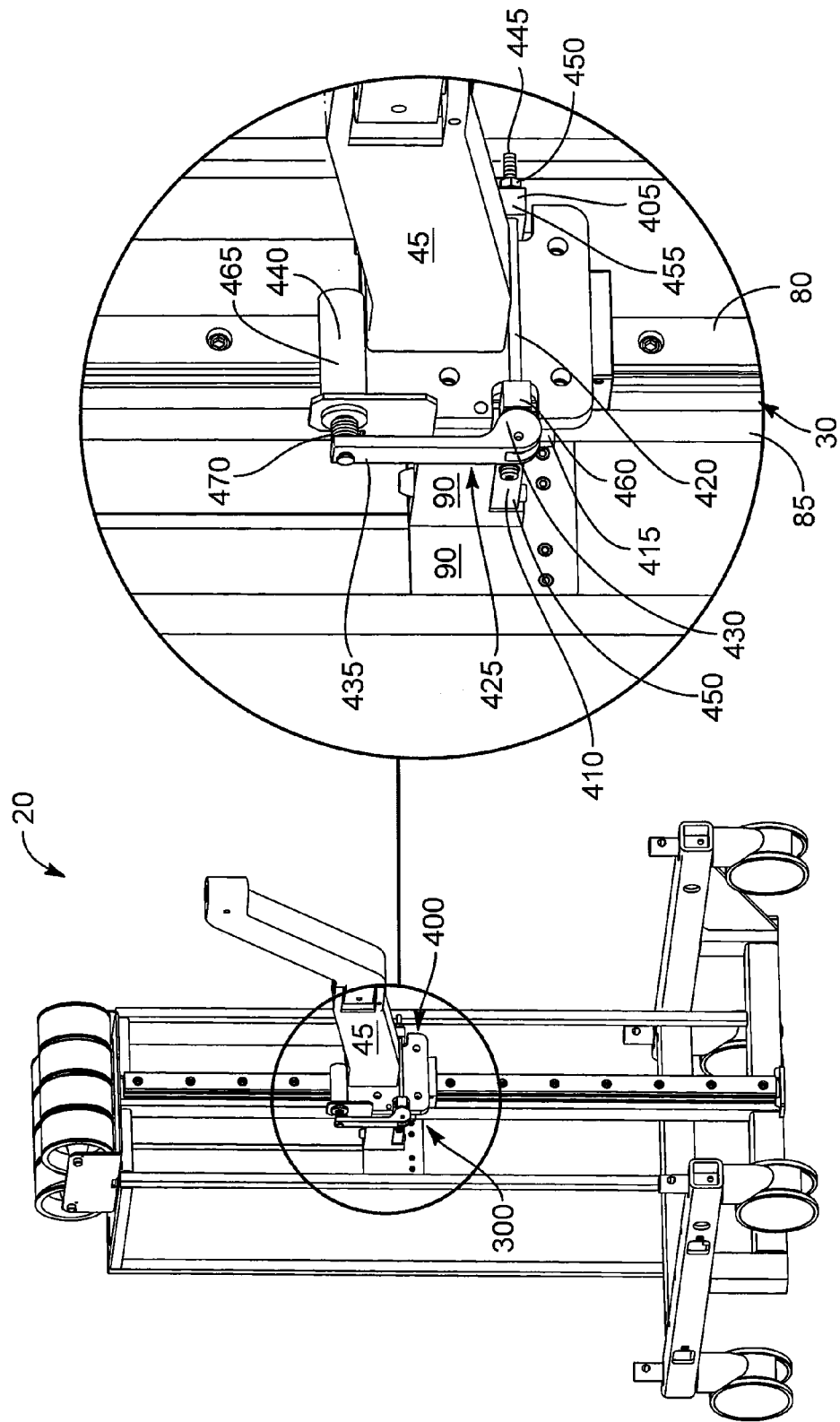
FIG. 10 shows a front perspective view of some embodiments of the C-arm positioning device where a C-arm X-ray device is not shown.
FIG. 11 shows a detailed view of a some embodiments of a brake system shown in FIG. 10.

FIGS. 10 through 16 illustrate some embodiments of suitable brake systems in which the brake systems comprise some embodiments of a V-brake 400. The V-brake 400 can comprise any suitable component that assists the braking function. For example, FIG. 11 shows some embodiments in which the V-brake 400 comprises a first 405 and second 410 pivotal brake arm where each are comprises at least one brake pad 415. The V-brake 400 can comprise a connector 420 that extends from the first pivotal brake arm 405, past the second pivotal brake arm 410, and to a connector lever 425 having a bias end 430 that is pivotally attached to the connector 420. FIG. 11 shows that the connector lever 425 comprises an elongated portion 435 that is connected to an actuator 440.

The V-brake 400 can function in any suitable manner that allows it to perform its braking function. In some configurations, when operating the actuator 440, the bias end 430 of the connector lever 425 forces the first 405 and second 410 pivotal brake arms to pivot towards each other so that the brake pads 415 physically and frictionally engage a portion of the linear bearing rail assembly 30 (e.g., the linear bearing rail 80 and/or spine 85). This movement at least momentarily stops or slows the substantially vertical motion of the linear bearing block 35 with respect to the linear bearing rail.

Figure 13:
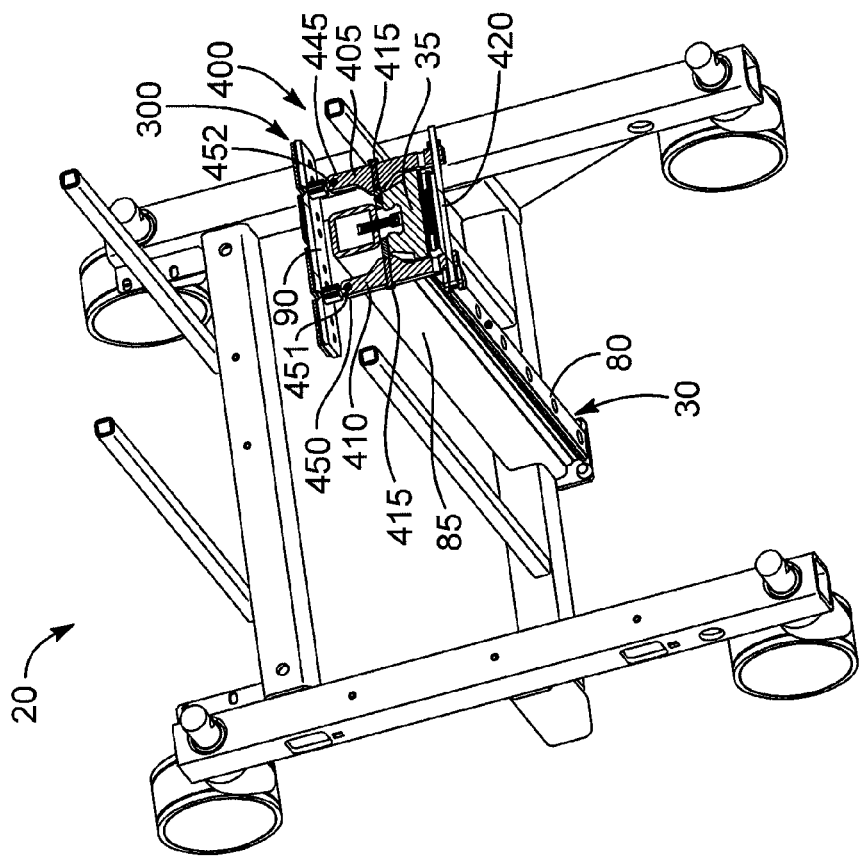
FIG. 13 shows a top cross-sectional perspective view of some embodiments of the brake system.
Figure 12:
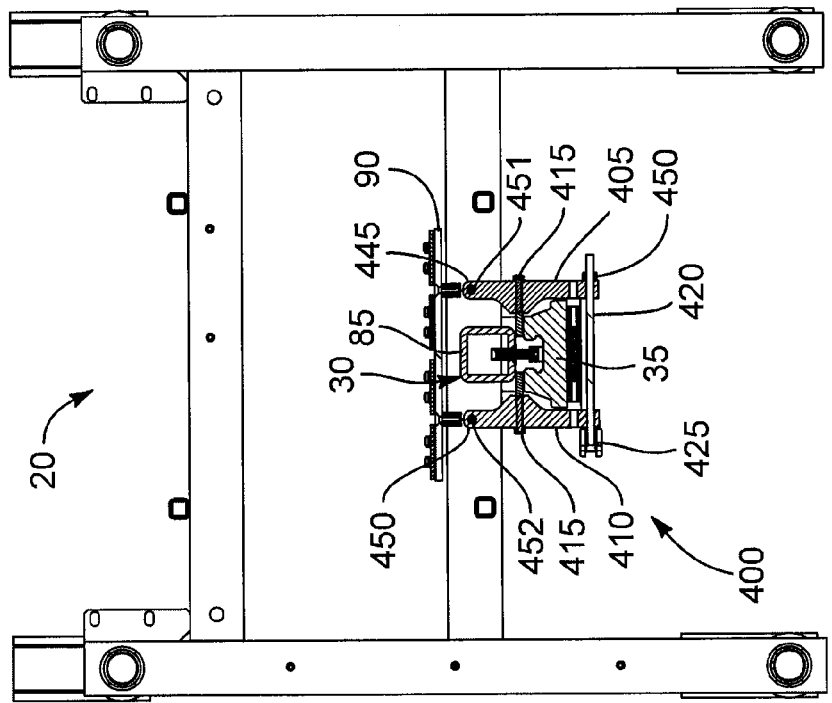
FIG. 12 shows a top cross-sectional plan view of some embodiments of the brake system.

The first 405 and second 410 pivotal brake arms can have any suitable characteristic that allows the brake system 300 to function as a brake. In one example, although the first and second brake arms can be attached to any suitable component of the C-arm positioning device 20. FIGS. 11 through 13 show some embodiments in which the first 405 and second 410 brake arms each have a first end (445 and 450, respectively) that is pivotally attached (e.g., via pivots 451 and 452) to the linear bearing block 35 (e.g., via the carriage 90). In another example, FIGS. 12 and 13 show that the pivotal brake arms (405 and 410) can be configured so their respective brake pads 415 can be positioned to contact a portion of the linear bearing rail assembly 30 when the brake arms are pivoted towards each other. In yet another example, FIGS. 11 and 12 show that the first 405 and second 410 pivotal arms can also be configured to allow the connector 420 to be anchored (e.g., via nut 450) to the first pivotal arm 405 and to extend past the second pivotal arm 410, allowing the second pivotal arm to slide past the connector as the connector lever 425 is rotated.

The brake pads 415 can contain any feature that allows them, when forced against a portion of the linear bearing block assembly 30 (or any other suitable surface), at least momentarily lock the movement (e.g., the substantially vertical movement) of the linear bearing block 35 with respect to the linear bearing rail assembly. Accordingly, the brake pads may comprise any suitable break pad material. Some examples of suitable brake pad materials include one or more types of an oil-impregnated sintered material (e.g., an oil impregnated sintered bronze and/or iron alloy), asbestos, a semi-metallic material, a metal, a ceramic, a rubber, a polymer, and/or any other suitable type of brake pad material. In some embodiments, however, the brake pad comprises an oil-impregnated sintered material, such as SUPER OILITE®, produced by Beemer Precision, Inc.

The connector 420 can comprise any suitable component that can be used to connect the first pivotal brake arm 405 to the connector lever 425 in a manner that allows the brake system 300 to function as described. For example, the connector can comprise a skewer, a shaft, a bolt, a cable, a chain, a linkage, and/or any other suitable component that can perform the connection function. FIG. 11 shows some embodiments in which the connector 420 comprises a threaded skewer 445 that can be tightened or loosened (e.g., via nut 450 or in any other suitable manner) to decrease or increase the spacing between the second ends (455 and 460) of the first 405 and second 410 pivotal brake arms.

The connector lever 425 can contain any component that allows it to force one or both of the pivotal brake arms (405 and/or 410) to pivot closer to the other. FIG. 11 shows some embodiments in which the connector lever 425 comprises a bias end 430 (e.g., an eccentric portion) that is pivotally attached to the connector 420 such that as the connector lever rotates, its bias end forces the first 405 and second 410 pivotal brakes arms to pivot towards each other and causes the brake pads 415 to contact a portion of the linear bearing rail assembly 30. In some embodiments, the connector lever can comprise an elongated portion 435 that is connected to an actuator 440.

Figure 14:
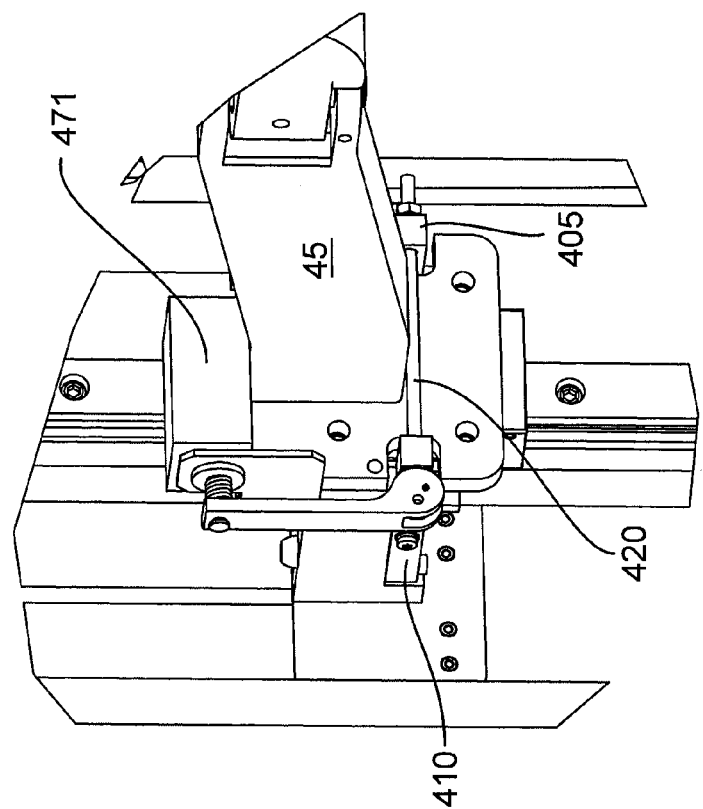
FIG. 14 shows a side perspective view of some embodiments of the brake system comprising a geared motor actuator.

The actuator 440 can comprise any suitable actuation device or assembly that is capable of selectively engaging and disengaging the V-brake 400. Some examples of suitable actuators comprise a solenoid actuator, a motor actuator (e.g., a geared motor actuator), a pneumatic actuator, a hydraulic actuator, a manual actuator, and/or any other suitable component or mechanism that can be used to selectively engage and disengage the V-brake. In some embodiments, FIGS. 10 and 11 show that the actuator 440 can comprise a solenoid actuator 465 having a spring 470. In these embodiments, when the actuator is disengaged, the spring forces the eccentric lever arm to an open position in which the V-brake system is disengaged. FIG. 14 shows other embodiments in which the actuator 440 comprises a geared motor 471. The geared motor can retain the V-brake 400 in an engaged position when power to the actuator is lost, while having a low power requirement and a small package size.

Figure 15:
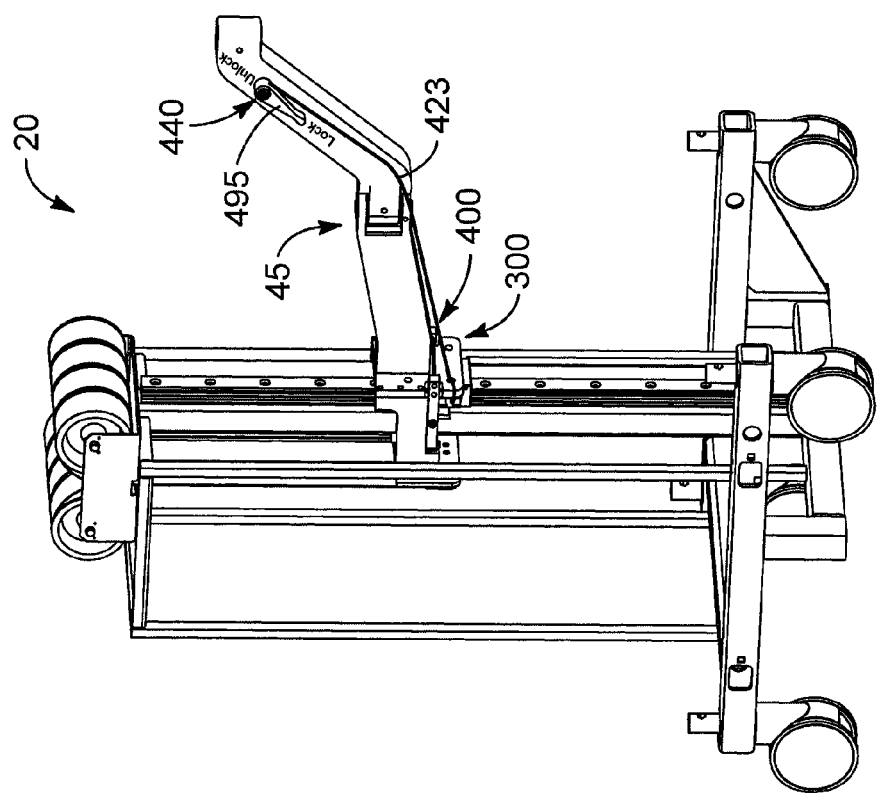
FIG. 15 shows a side perspective view of some embodiments of the brake system comprising a manual actuator.
Figure 16:
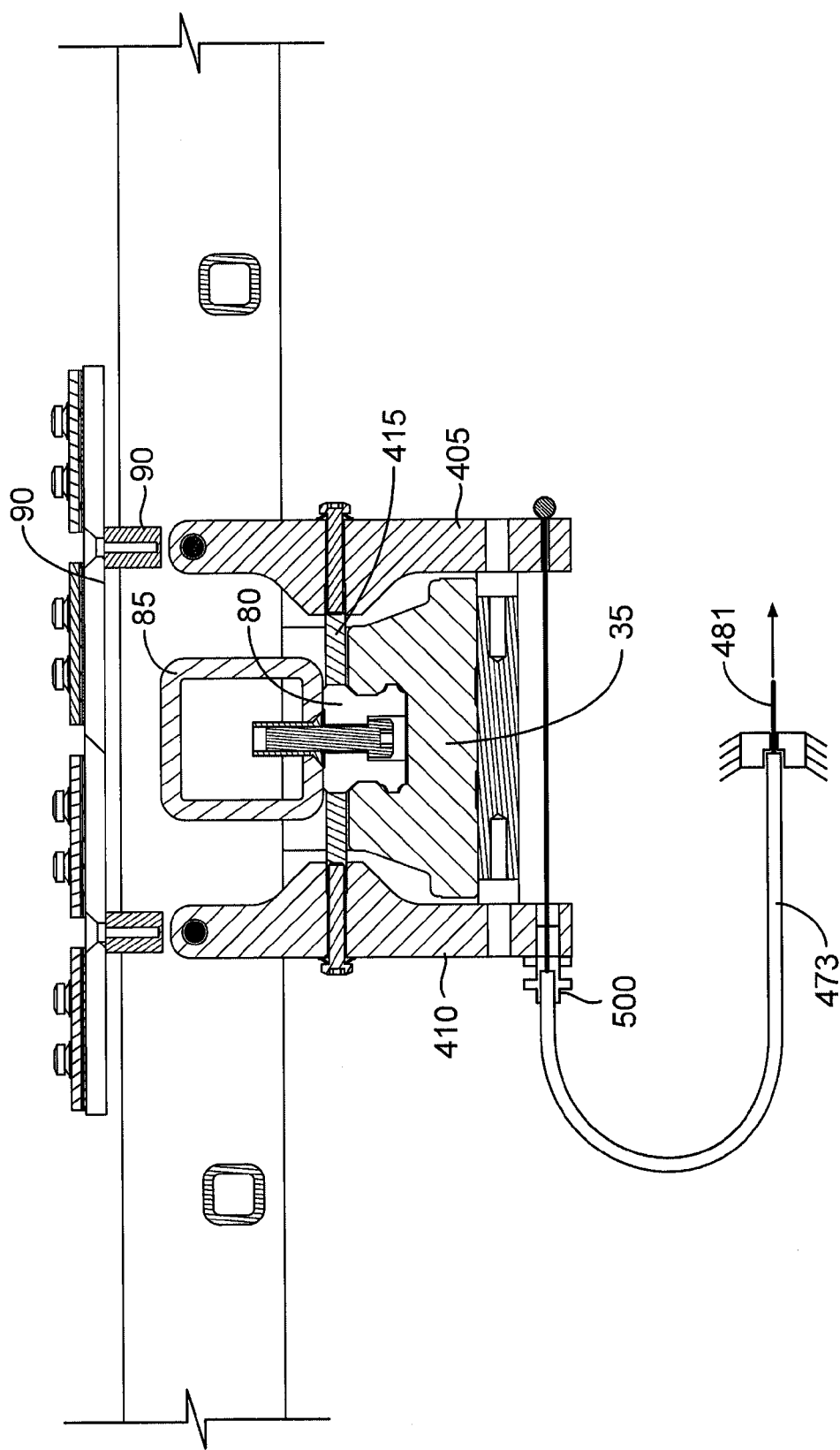
FIG. 16 shows a top cross-sectional view through some embodiments of the brake system that comprise the manual actuator.

The actuator 440 can be actuated in any suitable manner, including manually and/or electrically. In one example, the actuator can be manually actuated by forcing the eccentric brake lever 425 to a closed position, which engages the V-brake 400. In another example, FIGS. 15 and 16 show that a linkage (e.g., a cable 481, such as a cable in a sheath 473) can be pulled or pushed (e.g., via the movement of a lever 495, handle, or other actuator that is connected to the linkage) to move the pivotal brake arms 405 and 410 to a closed position to engage the V-brake. When actuated manually, the actuator can be disposed in any suitable position, such as on the C-arm support arm 45 as shown in FIG. 15.

Where actuated electrically, the actuator can be actuated in some embodiments through the use of a switch. The switch can comprise one or more tactile membrane switches, toggle switches, push-button switches, knife switches, single-pull single-throw switches, footswitches, and/or any suitable type of switch. FIG. 9 shows some embodiments in which the switch 480 comprises a push-button switch 485.

Where the actuator 440 is actuated by a switch, it can be disposed in any suitable location, including on the C-arm 25, on the C-arm support arm 45, on a wireless or a wired remote control, on a touch screen, on a foot pad, and/or any other suitable location. FIG. 9 shows some embodiments in which the actuator switch 480 is disposed on the proximal end 490 of the C-arm 25. In such embodiments, a user who is standing at the C-arm to reposition it, can selectively lock and unlock the vertical movement of the linear bearing block 35 while retaining his or her position by the C-arm.

The V-brake 400 can be modified to enhance its braking function. For example, while FIGS. 12 and 13 show some embodiments in which the V-brake 400 comprises 2 pivotal brake arms 405 and 410, the V-brake can be modified to comprise addition lever arms. In another example, the V-brake can be modified to comprise a single pivotal brake arm (e.g., the second pivotal brake arm 410) and a single opposing stationary arm (e.g., the first pivotal brake arm 405 can be replaced with a stationary arm). In this example, the break pad 415 can be disposed on the single pivotal brake arm so the pivotal brake arm can pivot to selectively lock and unlock the vertical movement of the linear bearing block 35.

While the actuator 440, brake pads 415, switch 480, and other components of the V-brake 400 have been described above with respect to the V-brake 400, they can be used with any other suitable type of brake system 300. For example, the described brake pads, actuator, switch, and/or other V-brake components can be used in any of the frictional or mechanical brake systems.

The brake system 300 (e.g., V-brake 400) can comprise any other suitable component(s). In some embodiments, the brake system can comprise a brake status indicator that indicates whether or not the brake is engaged. In one example of these embodiments, the switch 480 can act as a brake status indicator by being lit when the brake system is locked and unlit when brake system is unlocked, or vice versa. In another example, the brake system's status can be displayed on a monitor (e.g., monitor 170). In still another example, FIG. 15 shows an embodiment in which the brake status can be indicated by the position of a manual actuator 495.

The brake system 300 can optionally be configured to slip (or otherwise move) while in the engaged position, allowing the linear bearing block 35 to lower before a weight supported by the linear bearing block (e.g., a person leaning on the C-arm 25) causes the C-arm positioning device 20 to tip over. In these embodiments, the brake pad 415 comprises a material, such as an oil-impregnated sintered material, that is configured to slide across a portion of the linear bearing rail assembly 30 when a certain amount of vertical force is applied to the linear bearing block 35. The brake system can also be configured to slip when different amounts of weight are supported by the linear bearing block 35. Thus, the connector 420 can be shortened or tightened (e.g., via nut 450, length adjuster 500 in FIG. 16, etc.) and/or the actuator 440 can be adjusted to increase and/or decrease the range of movement of the connector lever 425 and/or brake lever arms 405 and 410.

The brake system 300 (e.g., V-brake 400) can be modified by optionally being attached to an uninterruptible power supply to ensure that the C-arm 25 can be raised or lowered if power from a power grid is lost. In the configurations containing a spring loaded solenoid design, this condition can be obtained even without such a power supply. As well, the brake system can be modified by so that the brakes could be applied if it was determined (i.e., via sensors) that a portion of the counterbalance load was lost (e.g., one of the constant force springs breaks).

The brake systems and C-arm positioning devices described above can be made in any suitable manner that forms the structures described. By way of example, the brake systems and C-arm positioning devices can be formed through a process involving molding, extruding, casting, cutting, stamping, bending, drilling, bonding, welding, mechanically connecting, and/or any other suitable process.

The brake systems described above can also be used by the operator to easily move the C-arm in an X-ray procedure. By way of example, an operator can raise and lower the C-arm 25 by applying an upward and downward force, respectively, to a portion of the linear bearing assembly 200. The operator can also engage the brake system to stop the vertical movement of the C-arm by actuating the actuator 440 (e.g., switching the switch 480). Similarly, to unlock the vertical movement of the C-arm, the operator can simply cause the actuator (e.g., via switch 480 or any other suitable manner) to disengage the brake system.

The described brake systems for C-arm positioning devices 20 have several features. First, unlike some conventional braking devices that are used to stop the vertical movement of a C-arm, the described brake system does not require an operator to engage the brake system by tightening a knob, which can be difficult to turn, be slow to engage and disengage, require the operator to lean over, require the operator to move, and/or be disposed in an inconvenient location. As a result, the described brake systems can be easier, faster, more convenient, and less distractive to use than some conventional brake systems.

As a second feature, because some embodiments of the brake system 300 allow the switch or other mechanism for actuating the actuator 440 to be disposed in a wide variety of locations, the described brake system may be more convenient to engage and disengage than some conventional brake systems. Accordingly, the described braking systems can be engaged and disengaged without requiring the operator who is moving the C-arm 25 to change positions.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. An X-ray positioning device, comprising:
   a substantially linear bearing rail assembly;
   an imaging arm comprising an X-ray source and an image detector, wherein a C-arm is connected to a linear bearing block and the linear bearing block is slidably coupled with the linear bearing rail to allow the imaging arm to move substantially vertically;
   a counterbalance mechanism that applies a force to the linear bearing block to substantially counterbalance at least a portion of the weight of the imaging arm and the linear bearing block; and
   a brake system that actuates to engage the linear bearing rail assembly to reduce or lock the movement of the linear bearing block.

2. The device of claim 1, wherein the counterbalance mechanism comprises a constant force spring.

3. The device of claim 1, wherein the engaged brake system slips to allow the linear bearing block to lower before a weight supported by the linear bearing block causes the X-ray positioning device to tip over.

4. The device of claim 3, wherein the brake system comprises an oil-impregnated sintered brake pad.

5. The device of claim 1, wherein the brake system comprises an actuator.

6. The device of claim 5, wherein the actuator is actuated electrically to engage the brake system.

7. The device of claim 6, wherein the actuator is selected from a motor, a solenoid, a pneumatic actuator, and a hydraulic actuator.

8. The device of claim 1, wherein the brake system comprises a V-brake.

9. An X-ray positioning device, comprising:
a substantially linear bearing rail assembly;
an imaging arm comprising an X-ray source and an image detector, wherein the imaging arm is connected to a linear bearing block and the linear bearing block is slidably coupled with the linear bearing rail to allow the imaging arm to move substantially vertically;
a constant force spring that applies a force to the linear bearing block to substantially counterbalance the weight of at least the imaging arm and the linear bearing block; and
a brake system that actuates to engage the linear bearing rail assembly to reduce or lock the movement of the linear bearing block.

10. The device of claim 9, wherein the linear bearing block has a stroke of more than about 10 inches.

11. The device of claim 9, wherein the engaged brake system slips to allow the linear bearing block to lower before a weight supported by the linear bearing block causes the X-ray positioning device to tip over.

12. The device of claim 11, wherein the brake system comprises an oil-impregnated sintered brake pad.

13. The device of claim 9, wherein the brake system comprises an actuator that electrically engages the brake system.

14. The device of claim 9, wherein the brake system comprises a manually-actuated actuator.

15. The device of claim 9, wherein the brake system comprises a brake status indicator.

16. An X-ray apparatus, comprising:
a mobile support structure; and
an X-ray positioning device comprising:
a substantially linear bearing rail assembly coupled to and supported by the mobile support structure;
an imaging arm comprising an X-ray source and an image detector, wherein the imaging arm is connected to a linear bearing block and the linear bearing block is slidably coupled with the linear bearing rail to allow the imaging arm to move substantially vertically;
a constant force spring that applies a force to the linear bearing block to substantially counterbalance the weight of at least the imaging arm and the linear bearing block; and
a brake system that actuates to engage the linear bearing rail assembly to reduce or lock the movement of the linear bearing block.

17. The apparatus of claim 16, wherein the engaged brake system slips to allow the linear bearing block to lower before a weight supported by the linear bearing block causes the X-ray positioning device to tip over.

18. The apparatus of claim 16, wherein the brake system comprises an oil-impregnated sintered brake pad.

19. The apparatus of claim 16, wherein the brake system comprises an actuator that electrically engages the brake system.

20. The apparatus of claim 16, wherein the brake system comprises a manually-actuated actuator.

21. The apparatus of claim 16, wherein the brake system comprises a brake status indicator.

22. A method for braking an X-ray positioning device, comprising:
providing an X-ray positioning device comprising:
a substantially linear bearing rail assembly coupled to and supported by the mobile support structure;
an imaging arm comprising an X-ray source and an image detector, wherein the imaging arm is connected to a linear bearing block and the linear bearing block is slidably coupled with the linear bearing rail to allow the imaging arm to move substantially vertically;
a constant force spring that applies a force to the linear bearing block to substantially counterbalance the weight of at least the imaging arm and the linear bearing block; and
a brake system that actuates to engage the linear bearing rail assembly to reduce or lock the movement of the linear bearing block; and
actuating the brake system to lock the vertical movement of the linear bearing block.

23. The method of claim 22, wherein the engaged brake system slips to allow the linear bearing block to lower before a weight supported by the linear bearing block causes the X-ray positioning device to tip over.

24. The method of claim 22, wherein the brake system comprises a switch that actuates the actuator and that is disposed at a location remote to the linear bearing block.

25. The method of claim 22, wherein the brake system comprises an actuator that engages the brake system, wherein the actuator is selected from a motor and a solenoid.

* * * * *